United States Patent [19]
Hobbs et al.

[11] Patent Number: 5,522,980
[45] Date of Patent: Jun. 4, 1996

[54] GAS SENSOR AND SENSING DEVICE

[75] Inventors: Bryan S. Hobbs, Surrey; John R. Finbow, Hampshire, both of United Kingdom; Leonard S. Raymond; David A. Rohrbacker, both of Tucson, Ariz.

[73] Assignee: Pima Sensors, Inc., Tucson, Ariz.

[21] Appl. No.: 401,959

[22] Filed: Mar. 10, 1995

[30] Foreign Application Priority Data

Mar. 24, 1994 [GB] United Kingdom .................. 9405899

[51] Int. Cl.$^6$ .................................................. G01N 27/26
[52] U.S. Cl. ........................... 204/432; 204/430; 204/431; 204/415; 422/83; 422/88; 422/98
[58] Field of Search ..................................... 361/502, 503, 361/504, 505, 506; 422/98, 88, 83; 204/415, 414, 421, 424, 431, 432, 430

[56] References Cited

U.S. PATENT DOCUMENTS

| | | | |
|---|---|---|---|
| 4,224,565 | 9/1980 | Sosmak et al. | 324/65 R |
| 4,350,660 | 9/1982 | Robinson | 422/90 |
| 4,429,343 | 1/1984 | Freud | 361/286 |
| 4,510,436 | 4/1985 | Raymond | 324/61 P |
| 4,571,543 | 2/1986 | Raymond | 324/425 |
| 4,768,012 | 8/1988 | Williams et al. | 338/34 |
| 4,822,566 | 4/1989 | Newman | 432/68 |
| 5,018,380 | 5/1991 | Zupancic | 73/23.2 |
| 5,102,525 | 4/1992 | Miyahara et al. | 204/415 |
| 5,143,696 | 9/1992 | Haas | 422/90 |
| 5,304,290 | 4/1994 | Hoffmann | 204/418 |

FOREIGN PATENT DOCUMENTS

| | | |
|---|---|---|
| 0061544 | 10/1982 | European Pat. Off. |
| 0341675 | 11/1989 | European Pat. Off. |
| 0426989 | 5/1991 | European Pat. Off. |
| 0523437 | 1/1993 | European Pat. Off. |

Primary Examiner—John Niebling
Assistant Examiner—Bruce F. Bell
Attorney, Agent, or Firm—Lee, Mann, Smith, McWilliams, Sweeney & Ohlson

[57] ABSTRACT

A gas sensor comprises a substrate on which are mounted three cells. Each cell includes an interdigitated capacitor defined by a pair of comb structure, electrically conductive tracks with the fingers of the combs interleaved. The tracks of each capacitor are covered by an insulating and chemically inert protective coating of an electrolyte. A monitor monitors one of a resistive component and a capacitive component of the relative dielectric constant of the electrolyte independently of the other component.

19 Claims, 7 Drawing Sheets

[G = 1/R]

GAS SENSOR AND SENSING DEVICE

FIELD OF THE INVENTION

The invention relates to a gas sensor and a gas sensing device for use in such a gas sensor.

DESCRIPTION OF THE PRIOR ART

Many types of gas sensor have previously been constructed based on a variety of principles including electrochemical cells and the like. One type of gas sensor relies on a capacitive measurement and an example is described in U.S. Pat. No. 4571543. In this case, a capacitive device is formed comprising an interdigitated electrode arrangement overlaid with an absorbent material, such as silicone rubber, which absorbs a gas to be sensed. This absorption causes the silicone rubber to expand and this causes a change in the capacitance of the capacitor which can be measured. One Of the problems with these known sensors is that at low concentrations it has been found that the monitored changes do not vary significantly which makes it very difficult to detect these low concentrations.

Another type of known gas sensor, particularly for carbon dioxide, includes a pair of electrodes immersed in an electrolyte defining a conductivity cell. When carbon dioxide enters the cell and dissolves in the electrolyte, the conductivity of the electrolyte increases and this can be monitored. This type of cell is disadvantageous in that problems can arise from corrosion and redox reactions at the electrodes.

SUMMARY OF THE INVENTION

In accordance with one aspect of the present invention, a gas sensor comprises a gas sensing device including a capacitor having spaced conductors associated with but electrically insulated from an electrolyte into which a gas to be sensed can dissolve and thereby change the relative dielectric constant of the electrolyte; and monitoring means for monitoring one of a resistive component and a capacitive component of the relative dielectric constant of the electrolyte independently of the other component.

We have devised a new form of gas sensor in which a gas to be sensed is caused to dissolve into an electrolyte and then either the capacitive or resistive component of the electrolyte is monitored independently of the other. We have found, particularly at low concentrations, that account must be taken of the fact that in a practical device, an electrolyte has a relative dielectric constant made up of both a capacitive and a resistive component. At low concentrations, the capacitive component is dominant and undergoes small changes which are very difficult to monitor. On the other hand, the resistive component changes much more rapidly with changes in gas concentration and by separating out at least one of these components from the other, a much more accurate measurement of gas concentration can be achieved.

An important feature of the invention is that the spaced conductors defining the capacitor plates are electrically insulated from the electrolyte. This ensures that there is no Faradaic contact between the conductors and the electrolyte so that no DC current will flow. This has the significant advantage of avoiding interference effects from redox reactions and corrosion etc.

In a simple example, just one of the resistance and capacitance could be monitored, preferably the resistive component. However, in a more complex example, the component which is monitored is dependent on the concentration to be measured. Thus, preferably resistance is monitored at low concentrations (e.g. up to about 20%) and capacitance at higher concentrations. Typically, means are provided to compare the capacitive component with a predetermined threshold and if it is less than the threshold then gas concentration is determined from the resistive component.

Various different ways may be used to implement the monitoring means. For example, Fourier analysis or a bridge circuit. It is useful to recognize, however, that in response to an applied alternating voltage, the resultant current (or voltage) from the capacitor will be made up of two components one of which (the capacitive component) lags in phase behind the other (resistive) component. This enables a technique such as synchronous detection to be used. An example of synchronous detection is described in U.S. Pat. No. 4822566. Thus, the monitoring means will comprise means for applying an alternating voltage to the capacitor and means for monitoring the resultant current from the capacitor in synchronization with the applied voltage. By monitoring the resulting current in phase with the applied voltage, the resistive component can be determined while monitoring the voltage 90° out of phase, the capacitive component can be determined.

Conveniently, means are provided to convert the current output from the capacitor to a voltage which is then applied to the monitoring means so that a voltage is monitored.

The capacitor could be provided by any conventional form of capacitor such as a parallel plate capacitor. Conveniently, however, the capacitor is formed by a planar interdigitated array of conductors defining an interdigitated capacitor (IDC). An IDC comprises a planar arrangement comprising two sets of interdigitated, elongate fingers, each set being connected to a respective conductor.

Various constructions for a gas sensing device incorporating an IDC can be utilized but in a preferred example, a gas sensing device according to a second aspect of the invention comprises a first interdigitated capacitor for connection to monitoring means, the capacitor including a set of interdigitated conductors, an electrically insulating coating provided over the conductors to prevent the electrolyte and gas contacting the conductors, and an electrolyte into which the gas to be sensed can dissolve, held adjacent the conductors and separated by the insulating coating, whereby the capacitance of the capacitor is affected by the electrolyte.

This device is compact and well suited for mass production.

The conductors are typically mounted on a supporting substrate which can be of any suitable, non-conducting material, for example ceramic, glass or plastic. Its thickness is not critical but will typically be of the order of 1 or 2 mm. The interdigitated conductors define the plates of the IDC and can be made of any material with a high electrical conductivity. Typically a metal is used, such as aluminium, copper, nickel or platinum. The width and spacing between the conductors are both typically 25 microns and it is preferred if these dimensions are smaller than the thickness of the electrolyte.

The insulating coating or layer is typically of ceramic, glass or plastic (polyimide) or other non-conducting, chemically inert materials. Its purpose is to decouple the conductors from the electrolyte and to prevent any electrochemical or chemical interaction between the conductors and electrolyte, for example corrosion and surface reactions between metal and electrolyte, interfering redox couples with chemical agents in the electrolyte, gassing such as hydrogen evolution, oxygen evolution or reduction, etc. These are particular problems with any electrolytes. The insulating coating should be impervious and continuous and thick enough to completely insulate and isolate the conductors from any contact with the electrolyte. Depending upon the material used, this could be of the order of a few microns to 10 or 20 microns.

The electrolyte could in principle be any material that reversibly absorbs the gas to be measured with an associated change in dielectric constant (as opposed to a dimensional change such as swelling).

In some cases, the electrolyte could be solid which has the advantage that it is easy to hold adjacent the conductors and minimises leakage problems. Examples of suitable solids are gels and polymers.

The electrolyte may also be a liquid and in that event the device further comprises means for restricting movement of the liquid electrolyte. In the case of carbon dioxide, for example, water is a suitable medium.

The electrolyte should be "thin" (for example 0.1 mm or less) to ensure fast equilibrium with the gas both on exposure and on removal of the test gas.

The means for restricting movement of the liquid electrolyte preferably includes a barrier layer positioned on the side of the liquid electrolyte opposite to the conductors of the IDC, the barrier layer preventing liquid leakage therethrough but permitting entry of gas into the liquid. For aqueous liquid electrolytes, porous PTFE is suitable which prevents liquid leakage and penetration through its pores, being hydrophobic, but allows easy gas access to the liquid due to its high gas diffusibility.

As has been mentioned above, it is preferable to use very thin films of liquid electrolyte. In the case of aqueous electrolytes, these can have difficulty penetrating the gap between the insulating coating or layer and the barrier layer. Preferably, therefore, at least one of the facing surfaces of the insulating coating and the barrier layer is liquid phillic, typically hydrophilic. Examples include the use of a conventional PTFE composite which is hydrophobic on one side and laminated with hydrophilic, porous materials on the other. In another example, the insulating coating may be composed of hydrophilic materials (sol gels etc) although thinner, more impervious layers can be achieved with other ceramics which have hydrophobic surfaces. These can be treated with inorganic or organic agents in very thin (not necessarily totally continuous, but essentially fairly complete coverage) such as sol gels, methyl cellulose, carboxymethyl cellulose etc.

It has been found in some cases that the barrier layer requires support since otherwise it exhibits orientation instability. Preferably, therefore, a porous support member is positioned in the gap defined between the barrier member and the insulated conductors. An example of a suitable support is a highly porous, fibrous, hydrophilic structure which supports the barrier or membrane but allows easy, unrestricted permeation by the liquid electrolyte. Such structures are provided by, for example, methyl cellulose, cellophane, carboxymethyl cellulose, glass matt, etc.

In the case of a liquid electrolyte, particularly an aqueous electrolyte, account must be taken of how to cope with evaporation and other changes due to changes of temperature and the like.

In one approach, additives such as ethylene glycol, polyethylene glycols, glycerol, sorbitol, agarose, etc can be added to the liquid electrolyte to prevent total desiccation in very dry ambient atmospheres. It has been found that these additives do not affect the sensor operation.

As an alternative, or in addition, the device may further comprise a cover member provided over the IDC and defining a gap between one or more apertures in the cover member and the barrier layer. The aperture(s) in the cover member do not affect gas entry because the device is an equilibrium based device with no current being generated. However, the apertures do minimise liquid (water) transpiration. Typically, the gap has a depth of about 1 mm.

The gap defined by the cover member is required to facilitate distribution of gas fluxes (inwards or outwards) over the surfaces of the barrier layer and therefore into or out of the liquid electrolyte. Preferably, a porous, highly diffusive, but rigid material is provided in the gap. This provides additional support to the barrier layer on its gas side while not impeding the spread of gas fluxes. Suitable materials are Vyon, Reticulated Vitreous Carbon (RVC) and the like.

A further modification which can be used alone or in conjunction with either of the other two modifications described above, and which copes with expansion and contraction of liquid electrolyte media, is to provide a reservoir in communication with the liquid electrolyte, the reservoir having associated vents to allow expansion or contraction of the liquid electrolyte. This enables pressure release of the space containing the liquid electrolyte without distortion of the IDC dimensions or leakage. The reservoir vents are preferably covered by a suitable liquid phobic material such as PTFE which allows free access of gases thus permitting the device to operate in any orientation. Typically, a liquid wicking material is provided in the reservoir to ensure that the vents are not fully covered with liquid in any orientation.

In some cases, the gas sensing device described above can be used by itself but such a device will normally need to be calibrated relatively frequently.

Preferably, a gas sensing assembly is provided comprising a gas sensing device according to the second aspect of the invention and a second gas sensing device substantially the same as the first gas sensing device but in which gas is prevented from accessing the electrolyte.

Providing a second device which is sealed from the atmosphere enables a base line measurement to be obtained and thus allows for certain effects to be compensated for such as general drift effects and the like.

Preferably, a common reservoir is provided for providing liquid electrolyte to both the first and second devices. In this way, any contamination of the electrolyte affects the second capacitor as well as the first.

In a most preferred example, the gas sensing assembly further comprises a third gas sensing device substantially the same as the first gas sensing device but which is constructed so that gas cannot reach the electrolyte and the electrolyte is insulated from the atmosphere. This third device is completely sealed from the atmosphere and the other device or devices and enables temperature compensation to be achieved. In a few cases, if the third device includes a reservoir, this could be vented. It should be understood that the use of second and third devices as described above is optional. Instead of or in addition to the second device an ion exchange resin could be provided in the reservoir to remove permanently absorbed ionic contaminants such as $SO_2$, $NH_3$, etc. while a temperature probe (e.g. thermistor) could be used in place of the third device.

BRIEF DESCRIPTION OF THE DRAWINGS

An example of a gas sensor according to the invention will now be described with reference to the accompanying drawings, in which.

DETAILED DESCRIPTION OF THE EMBODIMENTS

Figure 1:
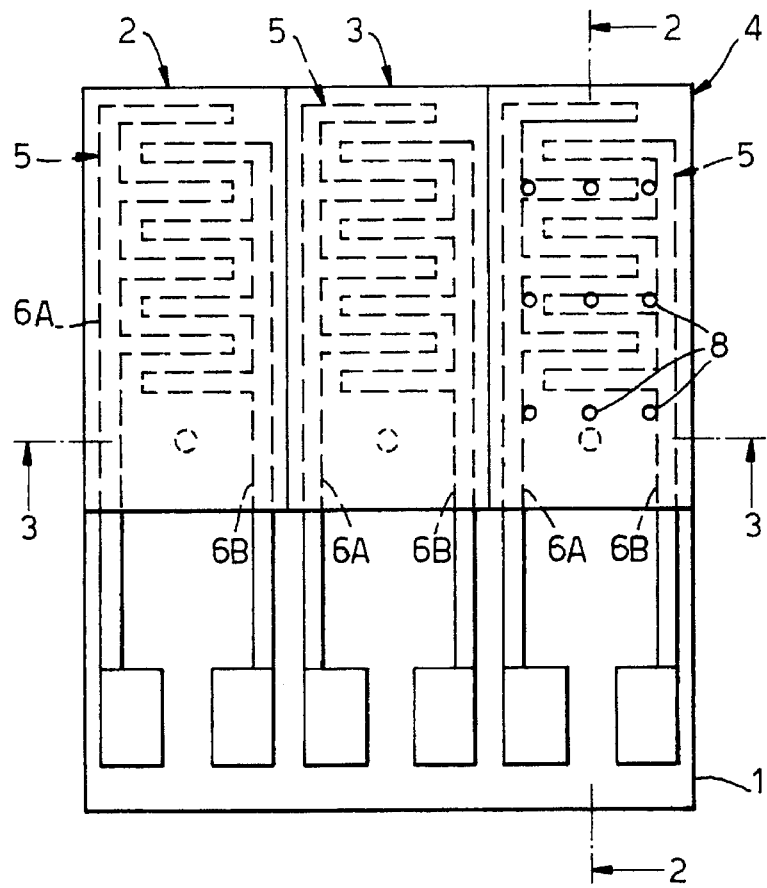
FIG. 1 is a plan of the sensor.
Figure 2:
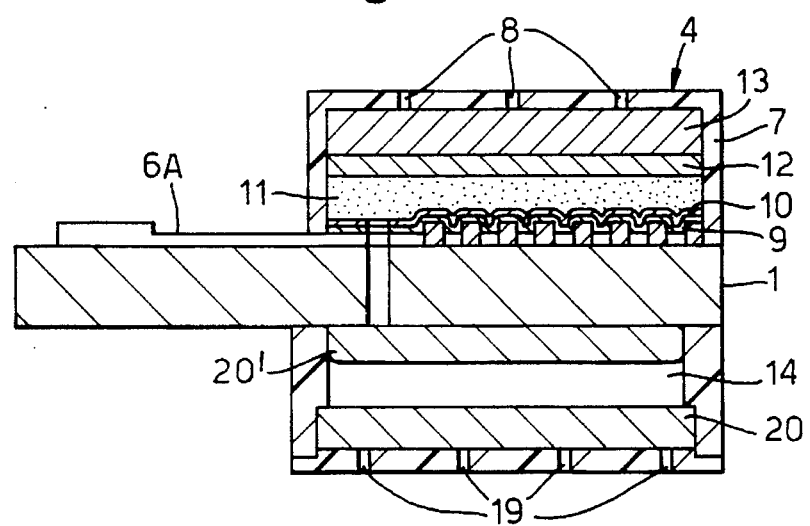
FIG. 2 is a section taken on the line 2—2 in FIG. 1.
Figure 3:
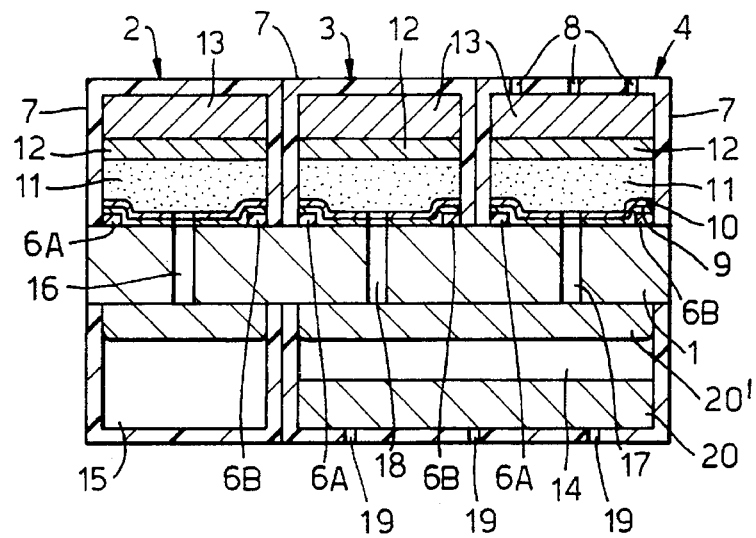
FIG. 3 is a section taken on the line 3—3 in FIG. 1.

The sensor shown in FIGS. 1 to 3 comprises a glass or plastics substrate 1 having a thickness of about 1 mm on which are mounted three cells 2–4. Each cell 2–4 includes an interdigitated capacitor (IDC) 5 defined by a pair of comb structure, electrically conductive tracks 6a,6b with the fingers of the combs interleaved. Typically, the finger width and finger spacing are each about 25 µm. The overall thickness of the tracks 6a,6b is about 0.2–0.3 microns.

Each cell 2–4 has a section covered by a plastics cover 7 having a cup shape, the cover 7 of the cell 4 having apertures 8 through which gas can enter the cell. The covers 7 of the cells 2,3 are closed.

The tracks 6a,6b of each IDC 5 are covered by an insulating and chemically inert protective coating of, for example, polyimide or a sol gel 9. The protective coating 9 is treated, as shown at 10, to provide a hydrophilic surface. The overall thickness of the coating 9 is about 0.5 microns.

A layer of cellophane 11 containing a thin film of water constituting an electrolyte is provided over the coating 9 in each cell 2–4. The thin film has a thickness of about 0.1 mm.

Each cell 2–4 is additionally provided with a polytetrafluoroethylene (PTFE) liquid barrier layer 12 to prevent water egress and a layer of Vyon 13 between the PTFE layer 12 and the top of the cover 7. The PTFE layer 12 has a thickness of about 0.15 mm and the Vyon layer 13 a thickness of about 1 mm. The thickness of the cover 7 is about 1 mm. The Vyon layer 13 and cellophane 11 support the PTFE layer 12.

Gas to be sensed enters the sensing cell 4 through the apertures 8 and enters the Vyon layer 13. The layer 13 causes the gas to spread out relatively evenly across the full area of the PTFE layer 12 through which it diffuses into the water in the cellophane 11. This diffusion is detected by the IDC as will be explained below and the resultant change of capacitance is detected.

It is important to allow for expansion and contraction of the thin film of water in the cellophane 11 and this is achieved by providing a pair of reservoirs 14,15 beneath the substrate 1. The reservoir 15 is in communication solely with the cell 2 via a conduit 16 extending through the substrate 1. The reservoir 14 is in communication with the cell 4 and the cell 3 through respective conduits 17,18. The reservoir 14 has a set of apertures 19 to allow for the passage of air and a layer of PTFE 20 to prevent water exiting through the apertures 19. The depth of the reservoirs 14,15 is about 3 mm. The reservoir 14 also includes a wick 20' on the underside of the substrate 1 to ensure the apertures 19 are always in contact with free space within the reservoir.

It will be noted that the cell 3 is subjected to similar conditions to the cell 4 except it is isolated from the gas to be sensed. This enables the cell 3 to provide a base line correction to the output from the cell 4. The cell 2 is completely isolated from all external conditions and can be used to achieve temperature compensation in a conventional manner.

Preferably, the water in each cell 2–4 is mixed with an anti-evaporation constituent such as ethylene glycol, glycerol or polyethylene glycol. Further, it is preferable to add an ion exchange resin to the reservoirs, particularly the reservoir 14 to remove permanently absorbed ions such as sulphites or ammonium ions.

The theory behind the sensor shown in FIGS. 1 to 3 will now be described in connection with a $CO_2$ sensor. The discussion will relate to a single cell but it will be appreciated the same theory applies to each of the cells 2–4.

Figure 4:
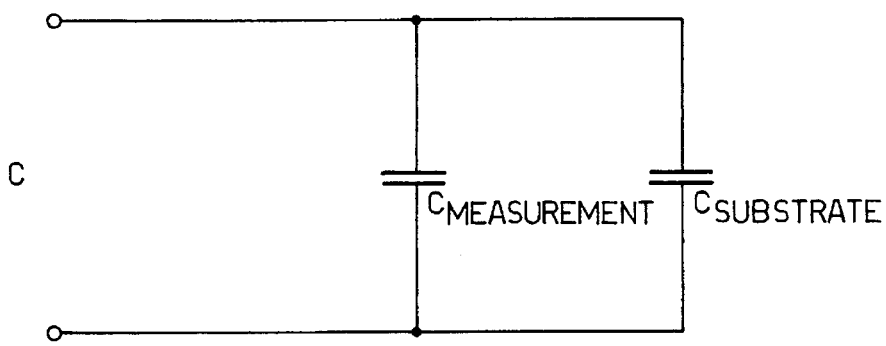
FIG. 4 is a circuit representation of one of the sensing cells shown in FIGS. 1–3.

The IDC can be considered to form two capacitors, one between the interdigitated fingers and the substrate, and the other above the substrate and including the insulating layer 9 and the electrolyte (water) 11. Drawn schematically, these two capacitors are in parallel as shown in FIG. 4.

We make the assumption that the substrate 1 is thick enough compared to the line width and spacing of the fingers so that it appears to be infinitely thick; therefore, we can determine its capacitance, which will then be a constant and not change. The capacitor above the substrate 1 does not necessarily have a constant dielectric value and can therefore change as a function of a variable.

Typically, the metal fingers of the IDC are 0.001 inches (25.4 µm) wide and the spacing between adjoining fingers is 0.001 inch (25.4 µm). The finger length is 0.120 inches, and there are typically 40 fingers on each side to give a vertical size of 0.160 inches (0.305×0.406 cm$^2$). (Area covered by IDC is 12.38×10$^{-6}$ m$^2$.)

Consider a unit area. The metal finger forms one plate of the unit capacitor and the interface between the insulating coating and the electrolyte form the second implied plate. The insulating layer 9 that covers the metal is the unit capacitor.

Resistance

Let us assume that the dielectric layer has a bulk resistivity of: $\rho = 1 \times 10^{14}$ Ω-m.

The equation for the resistance is $$R = (\rho d)/A \text{ ohms}$$

A is the unit area and d is the thickness of the insulating layer 9.

$$R = [(1 \times 10^{14})(5.0 \times 10^{-7})]/[6.452 \times 10^{-10}] = 7.75 \times 10^{16} \text{ ohms}$$

If we count the number of unit areas on one set of fingers, we get 4,960 units.

Since these would appear as parallel resistors, the equation will be:

$$R_{Total} = \{\Sigma_1^{4960}(1/R_i)\}^{-1} = 1.5625 \times 10^{13} \text{ ohms}$$

Capacitance

Given the same dimensions, the equation for the unit capacitance is:

$$C = \epsilon_r \epsilon_o A/d \text{ Farads}$$

where $\epsilon_r$ is the relative dielectric constant, and $\epsilon_o$ is $8.85 \times 10^{-12}$ F/m All of the unit area capacitances will be in parallel, so the total capacitance will be the number of unit cells, 4960, times the value of the unit capacitance.

$$C = [\epsilon_r(8.85 \times 10^{-12})(6.452 \times 10^{-10})(4,960)]/(5.0 \times 10^{-7}) = \epsilon_r(56.64)pF$$

Let us assume a value for the relative dielectric constant of $\epsilon_r = 4.0$.

Figure 5:
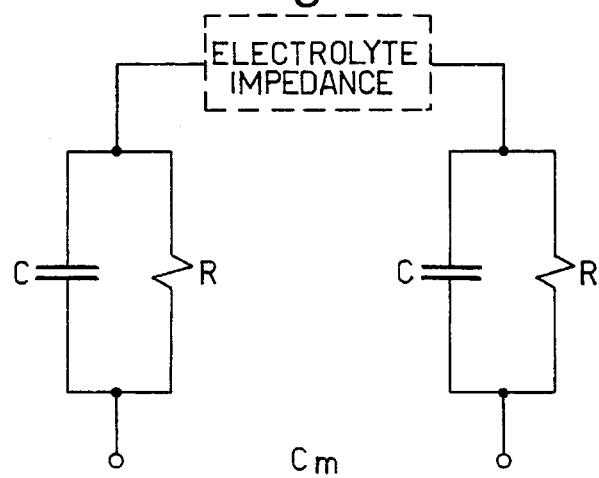
FIG. 5 is an electrical circuit representation of a pair of interdigitated fingers.

Then the total capacitance is 226.6 pF. The resistance, R, and the capacitance, C, are in parallel. There is an equivalent capacitor and resistor for each parallel set of interdigitated set of fingers, so the equivalent circuit would be as shown in FIG. 5. Note that the electrolyte will also form an impedance between the two series electrode circuits. A capacitor can also have an impedance which is frequency dependent. The impedance for the capacitor is given as:

$$Z_c = (1/\omega C)$$

where C is the capacitance in Farads and $\omega$ is equal to $2\pi$ times the frequency and is measured in radians per second. j is equal to the square root of $-1$.

$$Z_c = 1/j(2\pi \times 25,000)(226.6 \times 10^{-12}) = 28.1 \text{ Kohms } \angle -90°$$

The impedance of the capacitor is very small compared to the value of the resistor; we can neglect the value of the parallel resistors without changing any significant conditions in our analysis, and the results will be simplified.

IDC Capacitance

The capacitance of the interdigitated device is not just a simple parallel plate capacitor, but we have determined a very simple experimental formula that put it in term of the parallel plate equation; the equation is:

$$C_{IDC} = \{(4\epsilon_r \epsilon_o A)/(3d)\} \text{ Farads}$$

where A is the total area of one set of interdigitated fingers (one plate) and d is the line spacing between adjacent fingers.

$$C_{IDC} = \{[(4\epsilon_r)(8.85 \times 10^{-12})(6.462 \times 10^{-10})(4960)]/[(3)(25.4 \times 10^{-6})]\} \text{ Farads}$$

$A = (6.452 \times 10^{-10})(4,960) = 3.2 \times 10^{-6}$ m$^2$ $d = 25.4 \times 10^{-6}$ m $C_{IDC} = 1.4866\epsilon_r$ pF At room temperature, the relative dielectric constant of deionized water, DI-H$_2$O, is 80. The capacitance would then be:

$$C_{IDC} = 118.9 \text{ pF}$$

At this point, we have treated the IDC capacitance as an ideal capacitor which in fact it is not. The relative dielectric constant is a complex number which translates to the capacitor having a resistive component also. This is another way of expressing the resistive component that is in parallel with the capacitance. The resistive component is related to the conductance of the electrolyte, and it depends on the number of charged ions, their charge, and their effective velocity.

IDC Equivalent Circuit

Figure 6:
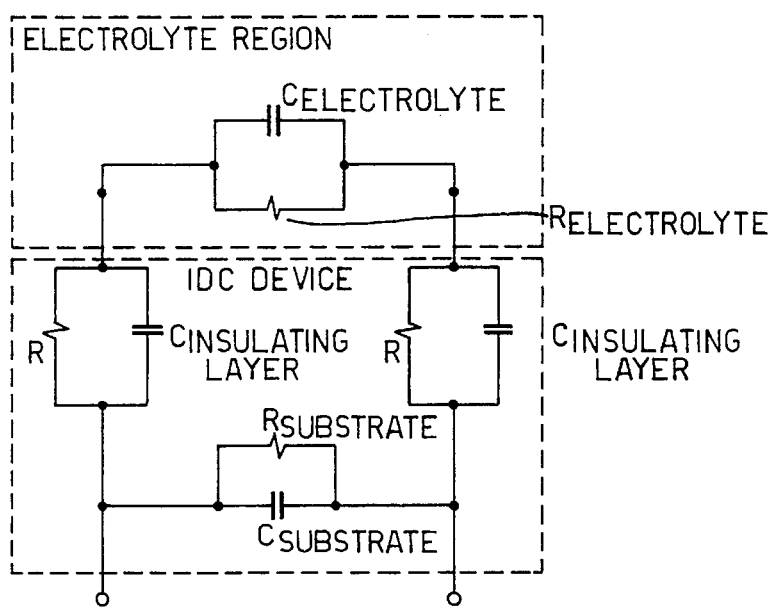
FIG. 6 illustrates the complete equivalent circuit of an IDC.

We have broken the IDC down into its component parts which allows us to see what effect each component will have on the total response of the IDC. FIG. 6 illustrates the complete equivalent circuit that we have developed.

Returning to the analysis for the IDC, we have the equation given above $$C = 1.4866\epsilon_r \text{ pF}$$

If we consider an IDC in air, we see that the capacitance is the result of the air above the top surface and the glass substrate which holds the device; these two capacitors are in parallel with each other. Typical measured values are around 8.8 pF.

$$C = C_{Air} + C_{Substrate}$$

Then $$C = (\epsilon_{Air} + \epsilon_{Substrate})(1.4866)pF$$

The relative dielectric constant for air is 1.00.

$C_{Air} = 1.4866$ pF $C_{Substrate} 8.8 - 1.4866 = 7.3$ pF

Giving $\epsilon_{Substrate} = 4.92$

Figure 7:
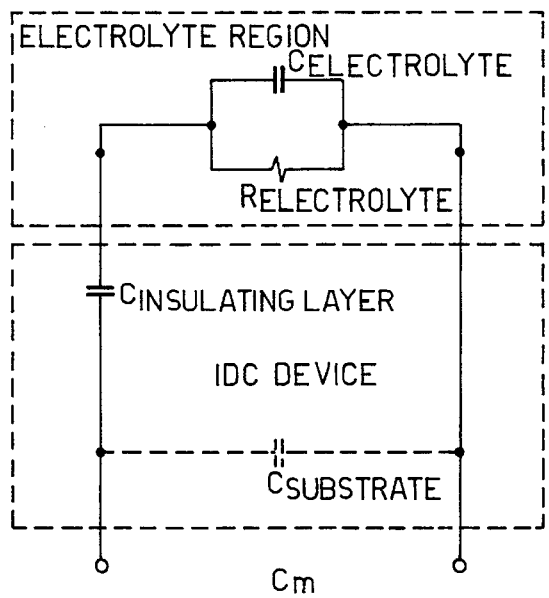
FIG. 7 is a reduced equivalent circuit derived from FIG. 6.

From the equivalent circuit shown in FIG. 7, we see that the substrate capacitance is in parallel with the insulating layer capacitance and the electrolyte capacitance.

The measured capacitance then becomes:

$$C_m = C_{Substrate} + [(1/0.5C_{insulating\ layer}) + (1/C_{Electrolyte})]^{-1} \text{ pF}$$

where the relative dielectric constant for $C_{Electrolyte}$ is a complex number and contains the conductance term.

If we neglect the substrate capacitance, then the insulating layer capacitance presents a maximum value that can be measured across the IDC. This can be seen by replacing $C_{Electrolyte}$ with a short circuit.

Complex Relative Dielectric Constant

Thus far we have used only the real part of the relative dielectric constant.

Consider the parallel resistor and capacitor in FIG. 7. Using complex notation, we can write the admittance (Y) of the circuit. (Admittance equals 1/impedance.)

$$Y = sC + G$$

or $$Y = s(C + G/S)$$

where $G = 1/R \Omega^{-1}$ $s = j\omega$ (Laplace Transform)

It is well known that:

$R = \rho d/A = d/\sigma A$ $G = \sigma A/d$

Then $Y = s(C + G/s)$ $Y = s\epsilon_o(\epsilon'A/d + \sigma A/s\epsilon_o d)$

Figure 8:
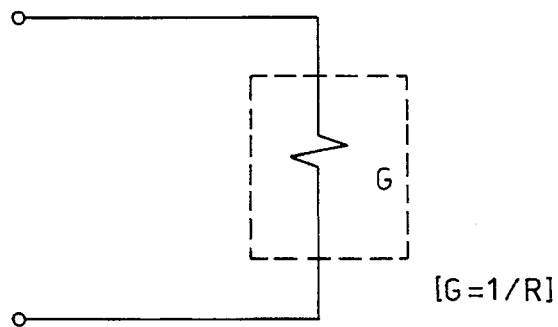
FIG. 8 is a circuit diagram of the resistive component of the IDC.

Let $$\epsilon^* = \epsilon_o(k' - jk'')$$

where $\epsilon^*$ is the complex relative dielectric constant, $k' = \epsilon_r$, and $k'' = \sigma/\omega\epsilon_o$ Then $\sigma/s\epsilon_0 = j\sigma/j(j\omega\epsilon_o) = -j\sigma/\omega\epsilon_o$ $\epsilon^* = \epsilon_o(k' - j\sigma/\omega\epsilon_o)$ where $\epsilon_o = 8.85 \times 10^{-12}$ Farads m$^{-1}$ $C^* = \epsilon^* A/d$ $Y = sC^* = j\omega\epsilon_o(k' - jk'')(A/d)$ $Y = j\omega\epsilon_o\epsilon_r A/d - j(j\sigma\omega A)/(\omega\epsilon_o d)$ $Y = j\omega\epsilon_o\epsilon_r A/d + \sigma A/d$ By using synchronous detection methods, we can separate the resistive effects from the capacitive effects. This will be demonstrated later. By separating out the resistive component, we have a new equivalent circuit shown in FIG. 8.

If we apply a voltage across the model, the current, I, that will flow is given by the equation:

$$I = VG \text{ Amperes}$$

This current will be in phase with the applied signal, V. Substituting for G, we get:

$$I = V[\sigma A/d] \text{ Amperes}$$

The values of A and d are fixed by the geometrical design of the IDC; therefore, the conductance term is a function of the variable $\sigma$.

Electrolyte

Let us assume that we have a liquid electrolyte that covers the IDC, i.e. the water film in the cellophane 11. What we will measure with synchronous detection will be the conductivity of the electrolyte. We now need to examine the factors that determine the conductivity of an electrolyte.

The general equation for the conductivity of an electrolyte is:

$$\sigma = F\Sigma(|Z_i|C_i u_i$$

where $F = 96,485$ C mol$^{-1}$ $|Z_i|$ = Absolute value of the charge of the $i^{th}$ ion $C_i$ = Concentration of the $i^{th}$ ion $u_i$ = Mobility of the $i^{th}$ ion We can now rewrite the current equation given above $$I = V[\sigma A/d] \text{ Amperes}$$

$$I = (VA/d)(F\Sigma|Z_i|C_i u_i) \text{ Amperes}$$

Henry's Law states that the solubility of an ideal gas in a liquid at a given temperature is directly proportional to the partial pressure of that gas.

This can be expressed in equation form:

Molality of a solute gas $= kP$ where $P$ = partial pressure of the gaseous solute $k$ = Henry's law constant, a constant characteristic of the solute and solvent.

Thus, the quantity of gas dissolved in water is related to the partial pressure of the gas in contact with the water.

If $CO_2$ is dissolved in water, we get:

$$CO_2 + H_2O \rightleftharpoons H^+ + HCO_3^{-1}$$

which increases the ionic content of the water.

The ionic concentration in the water is then a function of the partial pressure of the $CO_2$ exposed to the water. The conductivity could then be expressed in the terms of the partial pressure of the $CO_2$.

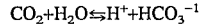

$$\sigma = \Psi F\{(|Z_H|[H^{+1}]u_H + |Z_{HCO3}|[HCO_3^{-1}]u_{HCO3}\}$$

where $\Psi$ is a cell constant for the IDC and $[C_i]$ is a function of the $CO_2$ partial pressure.

Then we have a current response given as:

$$I_r = (VA\Psi/d)(K[CO_2])$$

Figure 9:
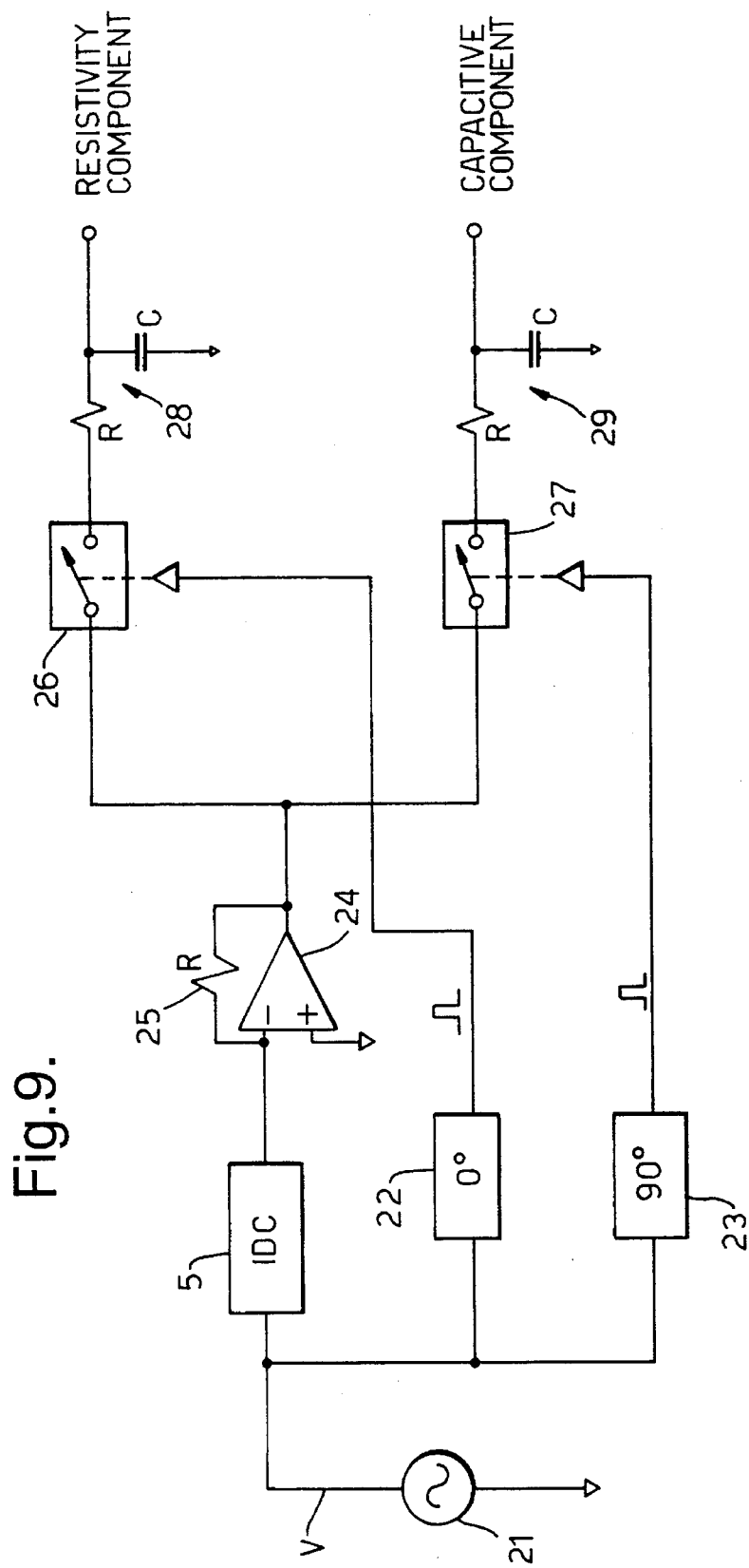
FIG. 9 is a block circuit diagram of the electrical components forming the sensor.

FIG. 9 illustrates a synchronous detection circuit which comprises a voltage oscillator 21 connected to the IDC 5 and in parallel to an in-phase sampling unit 22 and a 90° sampling unit 23. The output from the IDC 5 is fed to an inverting input of an operational amplifier 24 having a feedback resistor 25. The output from the amplifier 24 is fed to a sampling switch 26 and a sampling switch 27. The sampling switch 26 is actuated by the output from the in-phase sampling unit 22 and the sampling switch 27 is activated by the output from the 90° sampling unit 23. The output from each sampling switch 26,27 is fed to a respective integrator 28, 29 to constitute the resistivity component and capacitive component respectively.

The operational amplifier 24 acts as current-to-voltage converter. The current through the IDC 5 is dependent on the impedance of the device. If we assume only a capacitive component, we would have $$I = V * j\omega C$$

where I and V are both sine wave functions. Note that as the value of C increases, the current increases. If we extend the example to include a complex value of C (i.e. a capacitance and a conductance component), as either component increased, the current would increase. The current would, however, be out of phase with the applied voltage.

Figure 10:
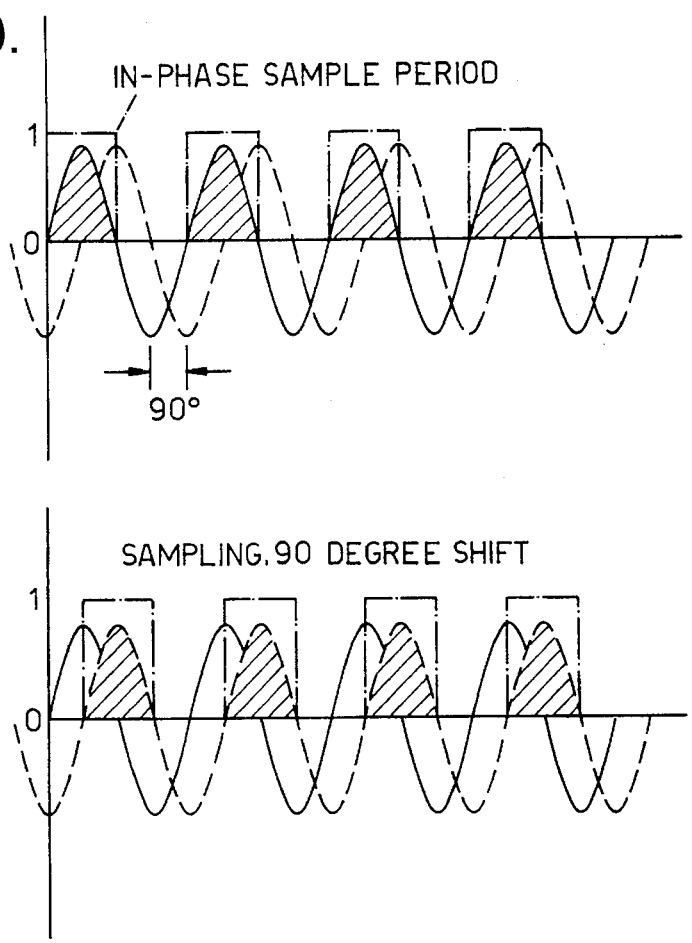
FIG. 10 illustrates the timing relationship between an input sine wave and square wave control or sampling signals.

In the circuit shown in FIG. 9, two square wave signals are generated along with the source sine wave. The timing relationship is shown in FIG. 10. The square wave signals are used to drive the analog switches 26,27 which sample the output of the current-to-voltage converter 24. The switching signals are sampled during the time that their value equals "1", and they are not sampling when the value is "0". Each sampling switch 26,27 is followed by an integrator 28,29 which integrates, or averages, the voltage over the time period that the switch is sampling, and the integrator holds the last value when the switch is not sampling. Note that the integrated voltage can be both positive and negative, but the resulting values are directly proportional to their respective components. The conductance is proportional to the "in-phase" signal.

In operation, circuits similar to that shown in FIG. 9 are provided for each of the IDCs 5 and the outputs from each circuit are fed to a processor (not shown). The processor monitors the capacitive component from the IDC of the cell 4 and providing this exceeds a threshold, indicating that the variation in capacitance is sufficiently great to be sensed, this capacitive component is used for further processing. Typically, this will involve obtaining the capacitive component from the cell 3 defining a base line and subtracting this from the capacitive component from the cell 4. An additional correction to take account of temperature changes could also be made by reference to the capacitive component from the cell 2. The resulting value is then compared to a calibration table which provides an indication of the gas concentration.

If the capacitive component is not greater than the threshold then the processor will use the resistivity component instead and go through a similar series of processing steps.

Some experiments have been carried out on cells constructed as described and the results are illustrated in FIGS. 11 to 15. The gas under test was carbon dioxide and air containing different concentrations of carbon dioxide was supplied to the sensor and the output determined and then plotted on the graphs shown.

Figure 11:
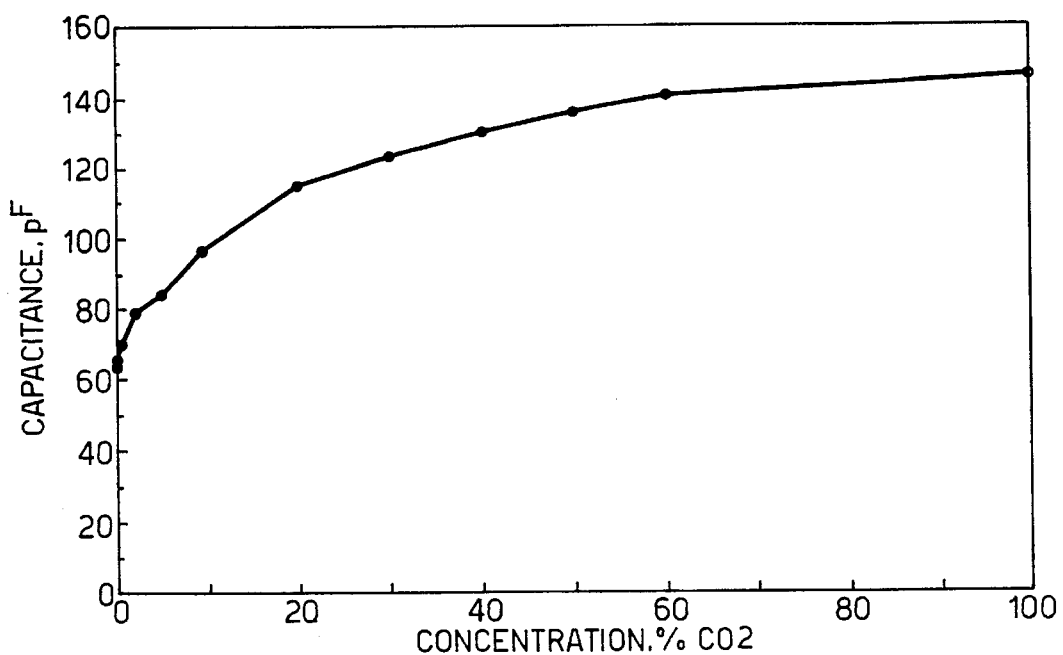
FIG. 11 illustrates graphically the variation of capacitance component with carbon dioxide concentration on a linear basis.
Figure 12:
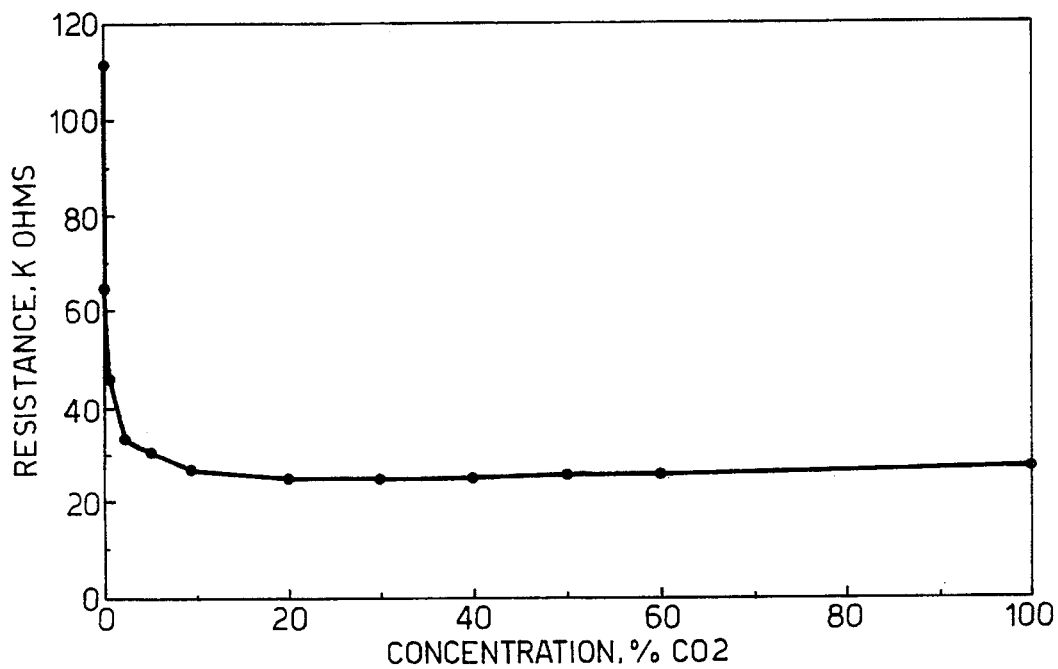
FIG. 12 illustrates the variation of the resistive component with carbon dioxide concentration on a linear basis.

FIG. 11 shows a linear plot illustrating how the capacitance component varies with $CO_2$ concentration. FIG. 12 is similar to FIG. 11 but showing variation of the resistance component. It can be seen from these graphs that a significant variation in capacitance occurs above about 10% concentration while for resistance a significant variation occurs only below about 10% concentration.

Figure 13:
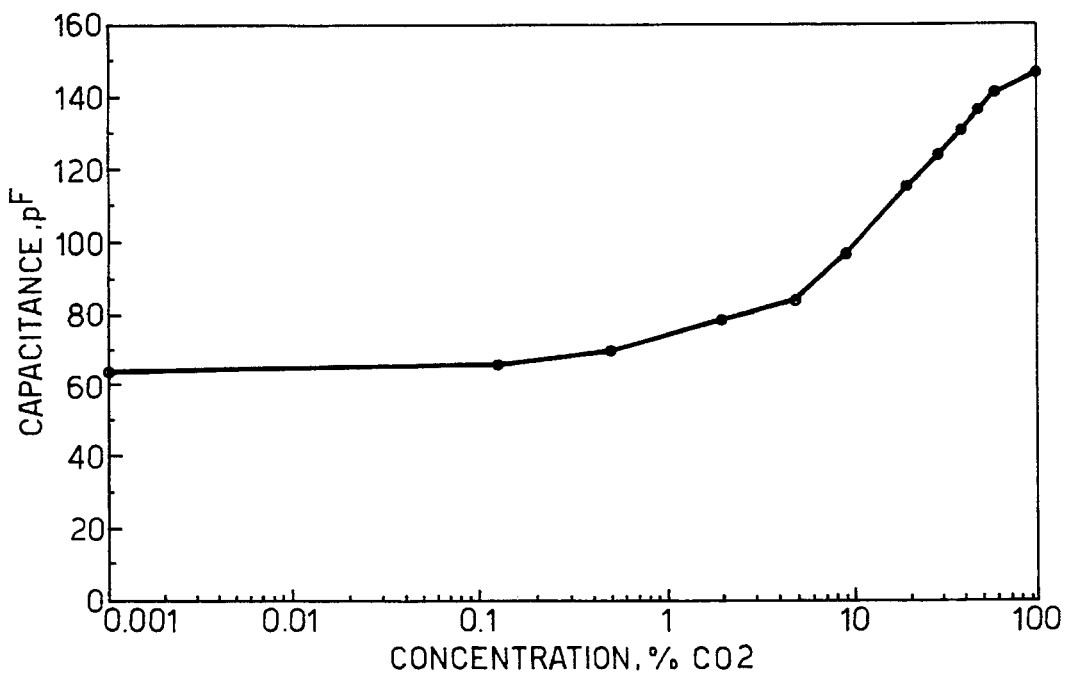
FIGS. 13 and 14 are similar to FIGS. 11 and 12 but with concentrations plotted on a logarithmic basis; and, FIG. 15 illustrates a portion of FIG. 14 in more detail.
Figure 14:
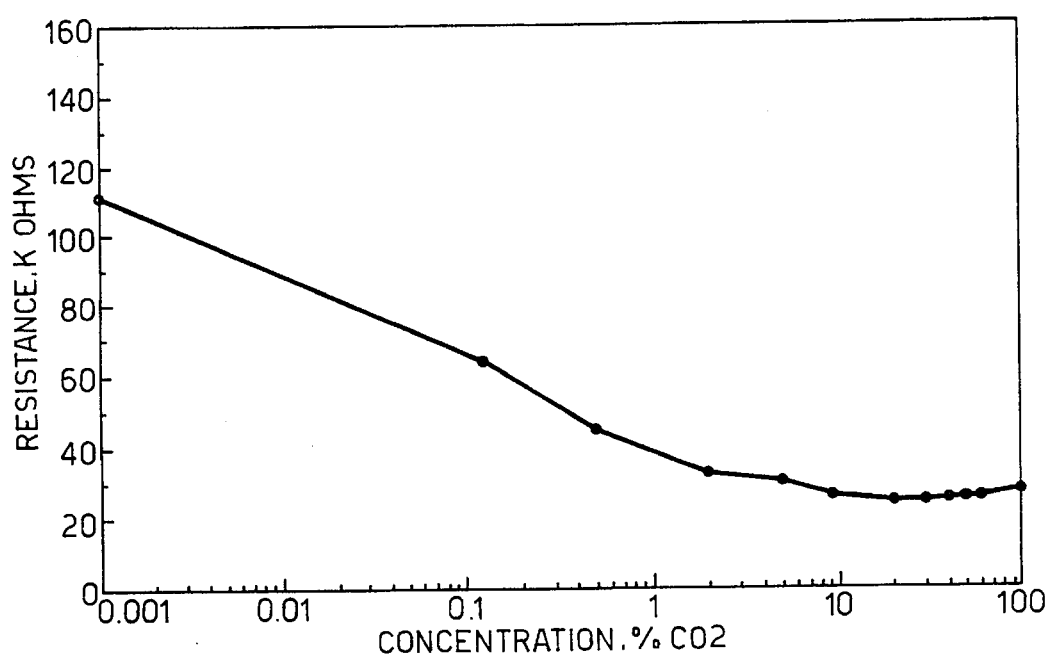

FIGS. 13 and 14 are logarithmic plots equivalent to FIGS. 11 and 12 respectively. Each of these shows that in the appropriate concentration range (above 10% for capacitance component and below 10% for resistance component) there is a substantially linear relationship with concentration.

Figure 15:
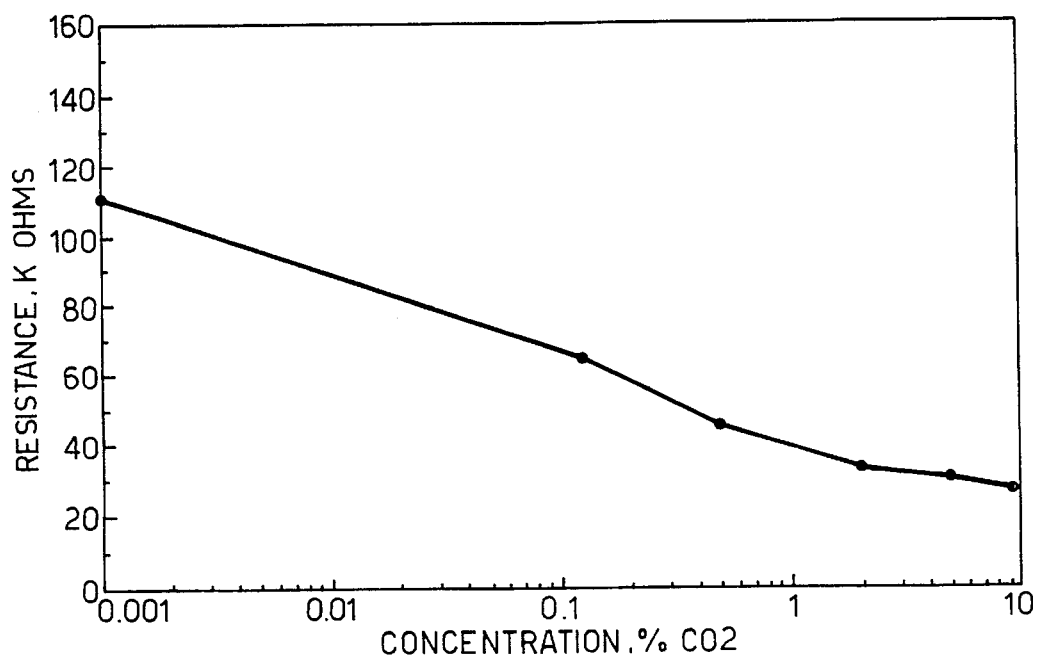

FIG. 15 illustrates part of FIG. 14 in more detail where the linear relationship on a logarithmic plot between concentration and resistance component can be seen more clearly.

We claim:

1. A carbon dioxide gas sensor comprising a gas sensing device including a capacitor having spaced conductors; an aqueous electrolyte defining a relative dielectric constant and into which carbon dioxide dissolves and thereby changes the relative dielectric constant of said electrolyte, and wherein said spaced conductors are associated with but electrically insulated from said electrolyte; means for holding said electrolyte adjacent said conductors; and monitoring means for monitoring one of a resistive component and a capacitive component of said relative dielectric constant of said electrolyte independently of the one of said resistive and capacitive components.

2. A sensor according to claim 1, wherein the monitoring means monitors only one of said resistive component and said capacitive component.

3. A sensor according to claim 1, wherein means are provided to compare the capacitive component with a set threshold and when said capacitive component is less than the threshold, to determine gas concentration from the resistive component.

4. A sensor according to claim 1, wherein said monitoring means comprises means for applying an alternating voltage to said capacitor to generate a resultant current and means for monitoring the resultant current from said capacitor in synchronisation with the applied voltage.

5. A sensor according to claim 4, wherein said means for monitoring the resultant current from said capacitor monitors said resultant current in phase with the applied voltage.

6. A sensor according to claim 4, wherein means are provided to convert the resultant current output from said capacitor to a voltage which is then applied to said monitoring means so that a voltage is monitored.

7. A sensor according to claim 1, wherein said capacitor is formed by a planar interdigitated array of conductors defining an interdigitated capacitor.

8. A carbon dioxide gas sensing device comprising a first interdigitated capacitor for connection to monitoring means, the capacitor including a set of interdigitated conductors, an aqueous electrolyte into which carbon dioxide dissolves, and an electrically insulating coating provided over said conductors to prevent the electrolyte and gas contacting the conductors, means for holding the electrolyte adjacent said conductors and separated by said insulating coating, wherein capacitance of the capacitor is affected by said electrolyte.

9. A device according to claim 8, wherein said electrolyte is in the form of a layer no thicker than 0.1 mm.

10. A device according to claim 8, wherein said means for holding said electrolyte adjacent said conductors includes a barrier layer positioned on a side of said aqueous electrolyte opposite to said conductors, the barrier layer preventing electrolyte leakage therethrough but permitting entry of gas into the electrolyte.

11. A device according to claim 10, wherein said insulating coating and said barrier layer define surfaces which face one another, and wherein at least one of the facing surfaces of the insulating coating and the barrier layer is hydrophilic.

12. A device according to claim 10, wherein a gap is defined between said barrier layer and said insulated conductors, and wherein a porous support member is positioned in said gap.

13. A device according to claim 12, wherein said porous support member is selected from the group consisting of methyl cellulose, cellophane, carboxymethyl cellulose, and glass matt.

14. A device according to claim 10, further comprising a cover member provided over said capacitor and defining a gap between one or more apertures in said cover member and said barrier layer.

15. A device according to claim 14, further comprising a porous, highly diffusive, but rigid material provided in the gap.

16. A device according to claim 8, further comprising a reservoir in communication with said aqueous electrolyte, said reservoir having associated vents to allow expansion or contraction of the electrolyte.

17. A carbon dioxide gas sensing assembly comprising a first gas sensing device comprising a first interdigitated capacitor for connection to monitoring means, the capacitor having a capacitance and including a set of interdigitated conductors, an aqueous electrolyte into which carbon dioxide dissolves, and an electrically insulating coating provided over said conductors to prevent the electrolyte and gas contacting the conductors, means for holding said electrolyte adjacent said conductors and separated by said insulating coating, wherein the capacitance of the capacitor is affected by said electrolyte; and a second carbon dioxide gas sensing device substantially identical to said first gas sensing device except that carbon dioxide is prevented from accessing said electrolyte.

18. An assembly according to claim 17, each device further comprising a reservoir in communication with said electrolyte, said reservoir having associated vents to allow expansion or contraction of the electrolyte, wherein a common reservoir is provided for providing electrolyte to both said first and second devices.

19. An assembly according to claim 17, further comprising a third gas sensing device substantially identical to said first gas sensing device except that it is constructed so that carbon dioxide cannot reach said electrolyte and said electrolyte is insulated from a surrounding atmosphere.

\* \* \* \* \*